United States Patent [19]

Howard

[11] Patent Number: Plant 5,359

[45] Date of Patent: Nov. 27, 1984

[54] GOLDEN SYCAMORE

[76] Inventor: Dave Howard, Rte. 1, Box 421, Burgaw, N.C. 28425

[21] Appl. No.: 465,874

[22] Filed: Apr. 8, 1983

[51] Int. Cl.[3] ..... A01H 5/12

[52] U.S. Cl. ..... Plt./51

[58] Field of Search ..... Plt./51

*Primary Examiner*—Robert E. Bagwill

[57] ABSTRACT

A sycamore tree having new foliage of a lemon-yellow color, turning yellow-green with maturity.

2 Drawing Figures

This specification relates to a new and distinct Sycamore (*Platanus occidentalis*) tree. More particularly, this tree produces foliage of a bright lemon yellow color. This color is exhibited in all the new leaf growth in the entire growing season. As the day length increases into summer with the incident increase in chlorophyll production, the older leaves change to a light yellow color.

As is well known, Sycamore (*Platanus occidentalis*) trees are planted for lumber and pulp wood production and in landscape plantings as shade trees. Also well known is their characteristic green to light green color which varies little from onset of new growth in the spring until chlorosis or frost causes change in the autumn.

This discovery provides a new variety of Sycamore (*Platanus occidentalis*) tree for use as an ornamental and a shade tree in landscape planting and site development. The distinctive lemon yellow color of the leaves that maintain this characteristic until early July in the Burgaw, N.C. latitude adds a new dimension to the use of shade trees in the color schemes of home, commercial and public site development.

This individual plant was discovered in a group of Sycamore (*Platanus occidentalis*) seedlings planted for shade tree production in 1981. Its origin is not known or traceable by the grower of the seedlings.

The following are the directly observable characteristics of the discovery;

LEAVES

The leaves are alternate, palmate veined with 3 to 6 lobes. No leaves have been observed with more than 6 lobes. The terminal leaves are bright yellow in color during the entire growing season. The upper and lower surfaces of the petiole, midrib and veins are yellow (near R.H.S. 7D). The stipule is hispid and encircles the stem. It is not fugacious. The petiole is round and measures 30 to 80 mm and is yellow in color in the early stages of growth, fading to light green in the later stages of growth. The leaves fade to light yellow in the summer and turn a brown to reddish color in the fall season. Supporting evidence for the color and shape of the leaf is furnished in two color photographs taken on July 5, 1982, which comprise the drawings.

STEMS

The stems are round in shape and brown to gray in color after the first year of growth. The growth of leaf and stem areas in the early leafing stage in spring is bright yellow as described in "lemon yellow". The stem fades to a light green as the growing season continues and changes to a gray to brown color over the dormant season. The pith of the stems is homogenous. The stems have lenticels.

WOOD

The density of the wood appears to be the same as for other Sycamore (*Platanus occidentalis*) trees. The short life of this individual plant and the necessity for protection from damage to insure continued survival have precluded investigation into the length of fibers, specific gravity or other characteristics of the wood.

FLOWER

No flowers have been observed in this two-year-from-seedling individual tree.

RESISTANCE TO DISEASE

No known diseases or disease symptoms have been observed.

REPRODUCTION

The tree has been reproduced by bud grafting on *Platanus occidentalis* stock and air layering. Other methods of reproduction have not been tried because of the necessity of maintaning this individual specimen in a vigorous and typical growth condition. Other means of asexual reproduction will be tried. Flowers—either pistillate or staminate—have not yet occurred. Observation to determine reproduction capability by sexual means will be continued.

TISSUE ANALYSIS

Blind samples of the stem and leaf tissue of the claimant Sycamore (*Platanus occidentalis*) tree, along with samples of other trees of this specie growing in adjacent rows, was submitted to the Agronomic Division, North Carolina Department of Agriculture, for analysis. No deficiencies in nutrients were found that would cause the continued yellow pigment production for two successive years. A copy of the plant analysis report is attached.

GROWTH RATE

This tree has a growth rate that is 60% to 80% of other Sycamore (*Platanus occientalis*) seedlings planted in the same field at the same time. This growth was approximately 7 feet the first year from a seedling of 18 to 24 inches. Other Sycamore (*Platanus occidentalis*) seedlings in the same setting grew to 8 to 11 feet the first year.

The following is indirectly deduced from stem and tissue analysis: Based on the tissue analysis, the conclusion of Mr. Bill Stanton of the North Carolina Extension Service, Forestry Division, is that the yellow color is genetically controlled. (See Plant Analysis Report attached.)

Having clearly described the distinctly new and different Sycamore (*Platanus occidentalis*) tree, what I claim is:

1. The Sycamore (*Platanus occidentalis*) tree herein described characterized by the lemon yellow color of its leaves and a slower growth rate.

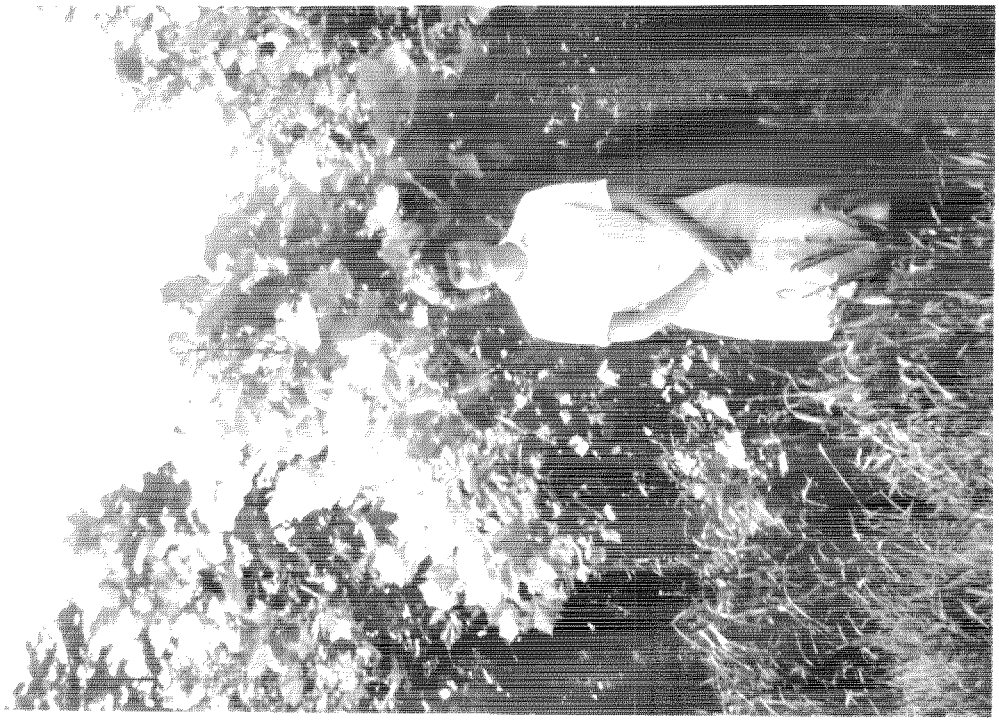
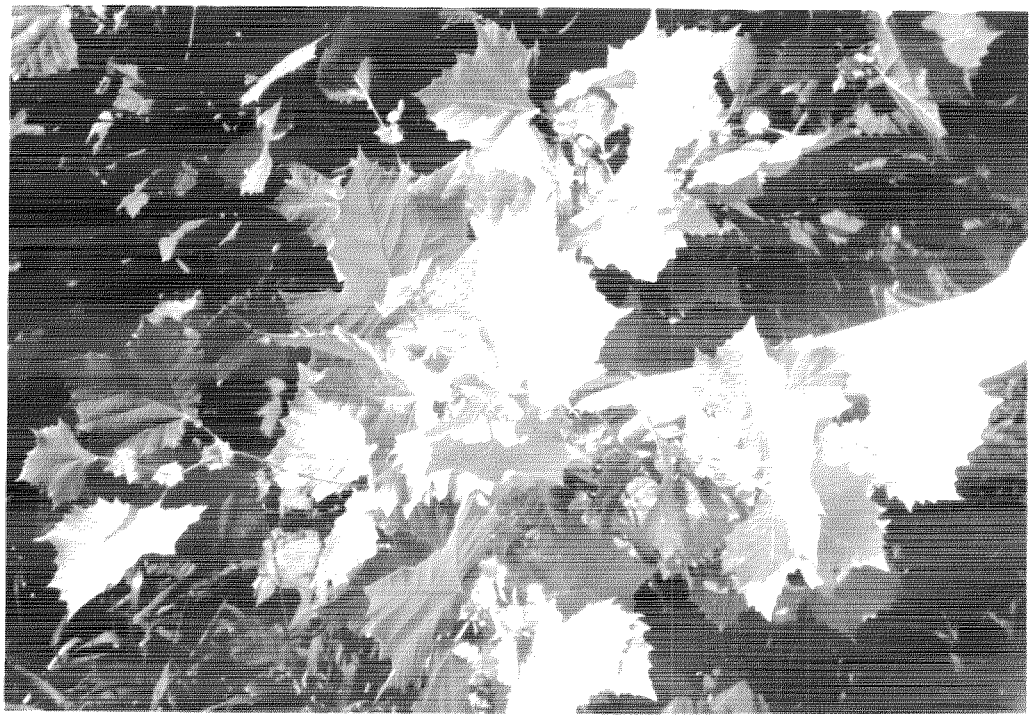

* * * * *